(12) United States Patent
Deaton, Jr. et al.

(10) Patent No.: US 7,800,762 B2
(45) Date of Patent: Sep. 21, 2010

(54) FIBER-BASED MID-INFRARED GENERATION LASER FOR LASER ULTRASOUND INSPECTION

(75) Inventors: John B. Deaton, Jr., Niskayuna, NY (US); Marc Dubois, Keller, CA (US); Kenneth R. Yawn, Weatherford, TX (US); Jeffery E. Maestas, Benbrook, TX (US); Thomas E. Drake, Jr., Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 1036 days.

(21) Appl. No.: 11/524,046

(22) Filed: Sep. 20, 2006

(65) Prior Publication Data

US 2008/0291963 A1 Nov. 27, 2008

(51) Int. Cl.
*G01B 11/02* (2006.01)
(52) U.S. Cl. ...................................... 356/502
(58) Field of Classification Search ................. 356/432, 356/498, 502
See application file for complete search history.

(56) References Cited

U.S. PATENT DOCUMENTS

| | | | |
|---|---|---|---|
| 5,930,030 A * | 7/1999 | Scifres | 359/341.3 |
| 6,335,943 B1 * | 1/2002 | Lorraine et al. | 372/28 |
| 6,810,052 B2 * | 10/2004 | Chicklis et al. | 372/39 |
| 7,203,209 B2 * | 4/2007 | Young et al. | 372/11 |
| 7,612,894 B2 * | 11/2009 | Drake et al. | 356/614 |
| 2005/0231735 A1 * | 10/2005 | Dubois et al. | 356/614 |
| 2007/0006658 A1 * | 1/2007 | Kennedy et al. | 73/622 |
| 2009/0010285 A1 * | 1/2009 | Dubois et al. | 372/3 |

* cited by examiner

*Primary Examiner*—Michael A Lyons
(74) *Attorney, Agent, or Firm*—Bracewell & Giuliani LLP

(57) ABSTRACT

Embodiments of the present invention relate to a laser system and method for the optical generation of ultrasound at a remote target. This involves generating a pump laser beam with a diode-pumped fiber laser. The diode pumped fiber laser is fiber-coupled with an optical fiber, either passive or diode pumped, to a generation laser head. The generation laser head generates a generation laser beam from the pump laser beam and directs the generation laser beam to the surface of the remote target. The interaction between generation laser beam and the surface of the remote target results in ultrasonic displacements at the remote target. These ultrasonic displacements may be sampled in order to assess and inspect the remote target.

20 Claims, 9 Drawing Sheets

FIBER-BASED MID-INFRARED GENERATION LASER FOR LASER ULTRASOUND INSPECTION

RELATED APPLICATIONS

This application incorporates by reference in its entirety for all purposes U.S. Provisional Application No. 60/091,240 filed on 30 Jun. 1998.

This application incorporates by reference in its entirety for all purposes U.S. Provisional Application No. 60/091,229 filed on 30 Jun. 1998 entitled "METHOD AND APPARATUS FOR DETECTING ULTRASONIC SURFACE DISPLACEMENTS USING POST-COLLECTION OPTICAL AMPLIFICATION" to Thomas E. Drake.

This application incorporates by reference in its entirety for all purposes U.S. patent application Ser. No. 10/753,208 filed on 7 Jan. 2004 and entitled "REMOTE LASER BEAM DELIVERY SYSTEM AND METHOD FOR USE WITH A ROBOTIC POSITIONING SYSTEM FOR ULTRASONIC TESTING PURPOSES" to Thomas E. Drake.

This application incorporates by reference in its entirety U.S. patent application Ser. No. 10/634,342 filed on 12 Feb. 2004 and entitled "METHOD AND APPARATUS FOR ULTRASONIC LASER TESTING" to Thomas E. Drake.

This application incorporates by reference in its entirety for all purposes U.S. Pat. No. 6,176,135 issued Jan. 23, 2001 and entitled "SYSTEM AND METHOD FOR LASER ULTRASONIC FREQUENCY CONTROL USING OPTIMAL WAVELENGTH TUNING."

This application incorporates by reference in its entirety for all purposes U.S. Pat. No. 6,335,943 issued Jan. 1, 2002 and entitled "SYSTEM AND METHOD FOR ULTRASONIC LASER TESTING USING A LASER SOURCE TO GENERATE ULTRASOUND HAVING A TUNABLE WAVELENGTH."

TECHNICAL FIELD OF THE INVENTION

The present invention relates generally to lasers, and more particularly, to a laser system used to generate ultrasonic surface displacements with fiber laser(s).

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must assess the structural integrity of composite materials. This assessment detects inclusions, delaminations and porosities. Conventional NDE methods are slow, labor-intensive, and costly. As a result, testing procedures adversely increase the manufacturing costs associated with composite structures.

Various methods and apparatuses have been proposed to assess the structural integrity of composite structures. One solution uses an ultrasonic source to generate ultrasonic surface displacements in a work piece which are then measured and analyzed. Often, the external source of ultrasound is a pulsed generation laser beam directed at the target. Laser light from a separate detection laser is scattered by ultrasonic surface displacements at the work piece. Then collection optics collect the scattered laser energy. The collection optics are coupled to an interferometer or other device, and data about the structural integrity of the composite structure can be obtained through analysis of the scattered laser energy. Laser ultrasound has been shown to be very effective for the inspection of parts during the manufacturing process.

However, the equipment used for laser ultrasound is custom-designed and is presently a limiting factor regarding inspection speed. Previous generation lasers used were either flash-lamp pumped rod architectures, diode-pumped slab configurations, or gas lasers.

Flash-lamp pumped lasers are limited to 100 Hz due to the important quantity of heat generated by the flash lamps that create important distortion in the laser media. Additionally, the life of those flash lamps is typically 100 million shots, requiring replacement every few weeks. Consequently, that type of laser is limited to laboratory applications or to applications where low repetition rates are acceptable. In typical ultrasonic inspection of composites, these lasers are slow and expensive to operate. Diode-pumped slabs are much faster (400 Hz is current limit and 1 KHz may be possible) but they use very expensive custom-manufactured diode arrays to pulse-pump the slabs and create a great amount of heat which can induce thermal distortion. Furthermore, diode array lifetimes have historically been a concern due to both high-cost, reliability and thermal distortion. High-power pulsed-diode pumping of a crystal slab introduces thermal distortions into the slab that ultimately limit the waveform quality of the generation laser beam. Wavefront distortion can limit the useful power of a laser and prevent efficient fiber optic delivery of the beam to the target. Heat removal is a significant design issue for both the diode arrays and the slab. Gas lasers can provide very large energy per pulse and possibly at repetition rates exceeding 400 Hz. However, gas lasers capable of such performances are bulky and heavy; their laser pulse parameters are difficult to adjust, and the emission wavelength cannot be modified outside a certain range. Gas lasers able to operate at repetition rates above 1000 Hz would be significantly heavier and bulkier. Another limitation of the gas lasers is the requirement of maintenance every one to three billion shots to change parts and to clean the optics.

It is important to note that all of the various ultrasound generation laser architectures described here are by their nature large and heavy. Therefore, these architectures are unsuited to use in portable laser ultrasound inspection systems for any sort of remote, in-the-field deployment. In addition, because they are so large and heavy, these architectures require substantial robotic fixturing and complex beam delivery systems even when they are deployed in factory environments, all of which greatly increases the initial overall cost of the laser ultrasound inspection system as well as the maintenance costs to keep the inspection system in operation in a production environment.

SUMMARY OF THE INVENTION

Embodiments of the present invention are directed to systems and methods that substantially address the above identified needs and other needs as well. The embodiments of the present invention are further described in the following description and claims. Advantages and features of embodiments of the present invention may become apparent from the description, accompanying drawings and claims.

Embodiments of the present invention provide a method to generate ultrasonic surface displacements at a remote target. This method involves generating a pump laser beam with a pump laser head that is itself a fiber laser. The beam from a fiber pump laser is delivered through an optical fiber, either passive or active, to a generation laser head. The generation laser head produces a generation laser beam with the input energy from the fiber pump laser beam. The generation laser head may then direct the generation laser beam to the surface of the remote target. The interaction between generation laser beam and the surface of the remote target results in ultrasonic displacements at the remote target. These ultrasonic displacements may be sampled in order to assess and inspect the remote target.

Yet another environment of the present invention provides a robotic composite inspection system operable to generate ultrasonic surface displacements on a surface of a remote target. This large area composite inspection system may be part of a large industrial robotic gantry based inspection system or use diode pumped fiber lasers to produce generation and/or detection laser beams and in so doing allow more compact robots and inspection systems to be built.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Figure 1:
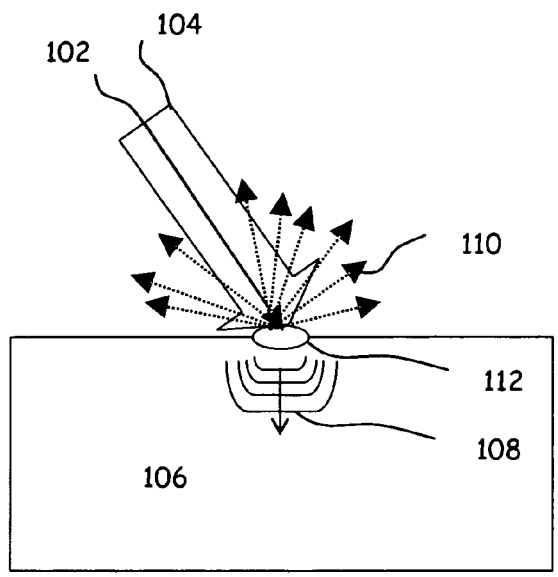
FIG. 1 illustrates the use of generation laser beam and a detection laser beam to generate and detect laser ultrasonic displacements in accordance with an embodiment of the present invention.

Preferred embodiments of the present invention are illustrated in the FIGURES, like numerals being used to refer to like and corresponding parts of the various drawings.

Embodiments of the present invention provide fiber lasers for use within a laser ultrasound system. Such an inspection system may employ multiple lasers. The primary task of a "first" detection laser is to illuminate the spot where a "second" laser is used to generate ultrasound in the part under test. The scattered light from the first laser is collected and analyzed with an interferometer to demodulate the surface vibrations caused by the return echoes of the ultrasound at the surface of the part. The detection laser (first laser) and generation laser (second laser) may use diode pumped fiber lasers to produce a high power output.

Embodiments of the present invention provide for faster inspection rates, improved system reliability, lower operation costs and enable mobile and portable systems. Flash-lamp-pumped lasers cannot operate at the repetition rates required for industrial applications of composite inspection. Diode-pumped slabs use very expensive custom-manufactured diode arrays to pulse-pump the slabs. High-power pulsed-diode pumping of a crystal slab may introduce thermal distortions into the slab that ultimately limit the waveform quality of the generation or detection laser beam. Wavefront distortion can limit the useful power of a laser and prevent efficient fiber optic delivery of the beam to the target.

Heat removal and thermal distortion becomes a significant design issue for both the diode arrays and the slab.

Gas lasers able to reliably operate at repetition rates above 1000 Hz would be very heavy and bulky. Another limitation of the gas lasers is the requirement of maintenance every one to three billion shots to change parts and to clean the optics.

An all-fiber pump laser scheme may use many small continuous wave (CW) diode lasers ('pump diodes') to pump the doped active laser fiber. This has several advantages. First of all, these low power diodes offer the very high reliability required for telecom applications and have mean time between failure (MTBF) ratings of 100,000 hours. Also, all of the fiber-coupled pump diodes are relatively small in power (typically only a few watts) and the failure of any one would have little impact on the total performance of the fiber laser.

Furthermore, thermal management of a fiber laser/amplifier is more easily handled than within a traditional bulk crystal gain medium. Heat removal from the fiber-coupled pump diodes is managed separately from the gain medium (the doped active laser fiber), and the ratio of the fiber surface area (where heat is extracted) to the volume is many orders-of-magnitude larger than the surface-to-volume ratio for a rod or slab laser architecture. As a result, a fiber laser can be operated in a fundamental (TEM00) transverse mode with very little wavefront distortion ($M^2<1.2$). Fiber lasers do not use traditional discrete or bulk optics such as mirrors or lenses. Therefore contamination issues within the laser cavity are eliminated. This is particularly advantageous for industrial inspection systems that run around the clock in production applications. A fiber laser looks like a piece of industrial electronics. Flexible architecture enables mobile and possibly portable laser ultrasonic inspection equipment designs. Overall, fiber lasers are well suited for harsh industrial environments.

FIG. 1 depicts two incoming laser beams that generate and detect laser ultrasonic displacements as provided by embodiments of the present invention. Laser beam 102 generates ultrasound while illumination (detection) laser beam 104 detects the ultrasound at a remote target 106, such as a composite material under test. As shown, these lasers may be coaxially applied to remote target 106. Generation laser beam 102 causes thermo-elastic expansion 112 in target 106 that results in the formation of ultrasonic deformations or waves 108. Deformations or ultrasonic waves 108 propagate in target 106 and modulate, scatter and reflect illumination laser beam 104 to produce phase-modulated light 110 directed away from target 106 which is collected and processed to obtain information describing the internal structure of remote target 106.

Figure 2:
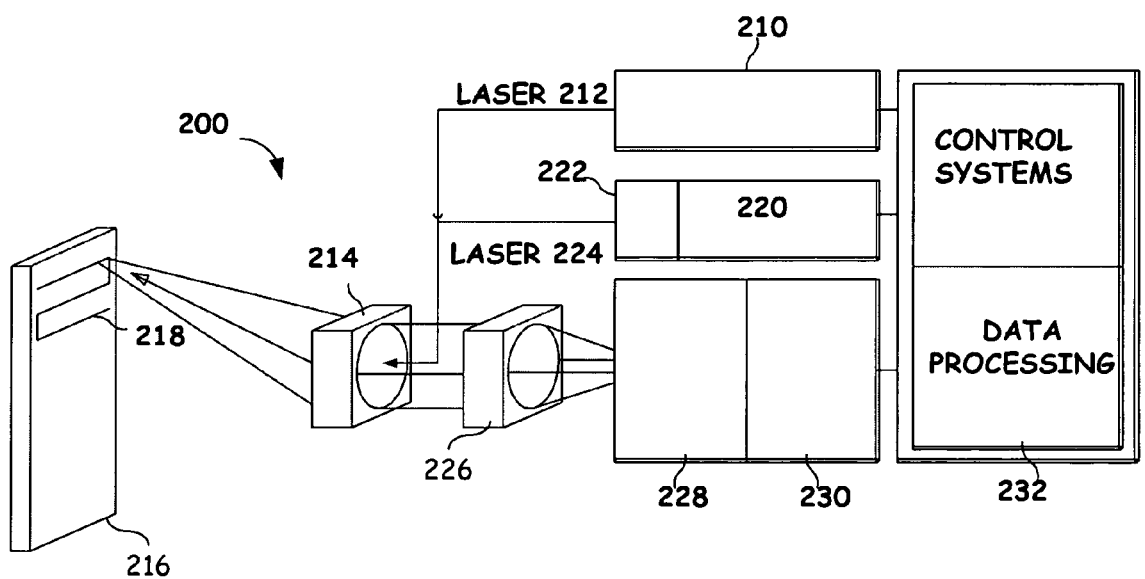
FIG. 2 provides a block diagram to show the basic components of laser ultrasound system.

FIG. 2 provides a block diagram with the basic components for performing ultrasonic laser testing. Generation laser 210 produces generation laser beam 212 which optical assembly 214 directs to target 216. As shown, optical assembly 214 includes a scanner or other like mechanism that moves laser beam 212 along a scan or test plan 218. Optical assembly 214 may include visual cameras, depth cameras, range detectors, narrowband cameras or other like optical sensors known to those having skill in the art. These optical sensors each may require calibrations prior to performing an inspection. This calibration verifies the ability of the system to integrate information gathered by various sensors. Generation laser 210 produces an ultrasonic wave 108 within target 216. Generation laser 210 will be described in further detail with reference to FIG. 3A and following.

The ultrasonic wave 108 is the result of thermo-elastic expansion 112 of the composite material as the composite material absorbs the generation laser beam. Composite material 216 readily absorbs generation laser beam 212 without ablating or breaking down. Higher powered generation lasers are not necessarily preferred to overcome signal-to-noise ratio (SNR) issues as these can result in ablation of material at the surface of the workpiece, potentially damaging the component. In other embodiments, depending on the material being tested, some ablation may be acceptable in order to increase the SNR of the detected signal. Generation laser beam 212 has appropriate pulse duration, power, and frequency to induce ultrasonic surface deformations. For example, a transverse-excited atmospheric (TEA) $CO_2$ laser can produce a 10.6 micron wavelength beam for a 100 nanosecond pulse width. The power of the laser must be sufficient to deliver, for example, a 0.25 joule pulse to the target, which may require a 100 watt laser operating at a 400 Hz pulse repetition rate. Generation laser beam 212 is absorbed as heat into the target surface thereby causing thermo-elastic expansion without ablation.

Illumination or detection laser 220 operating in pulsed mode or CW mode does not induce ultrasonic displacements. For example, an Nd:YAG laser can be used. The power of this laser must be sufficient to deliver, for example, a 100 millijoule, 100 micro-second pulse, which may require a one kilo-watt (KW) laser. Illumination (detection) laser 220 generates detection laser beam 222. Illumination laser 220 includes or optically couples to filtering mechanism 224 to remove noise from detection laser beam 224. Optical assembly 214 directs illumination laser beam 224 to the surface of composite material 216 which scatters and/or reflects detection laser beam 224. Resultant phase modulated light is collected by collection optics 226. As shown here, scattered and/or reflected detection laser light travels back through optical assembly 214. Optional optical processor 228 and interferometer 230 process the phase modulated light to produce a signal containing information representative of the ultrasonic displacements at the surface of composite material 216. Data processing and control system 232 coordinates operation of the laser ultrasound system components.

Data processing and control system 232 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 232 executes, operational instructions corresponding to at least some of the steps and/or functions as will be illustrated.

Figure 3A:
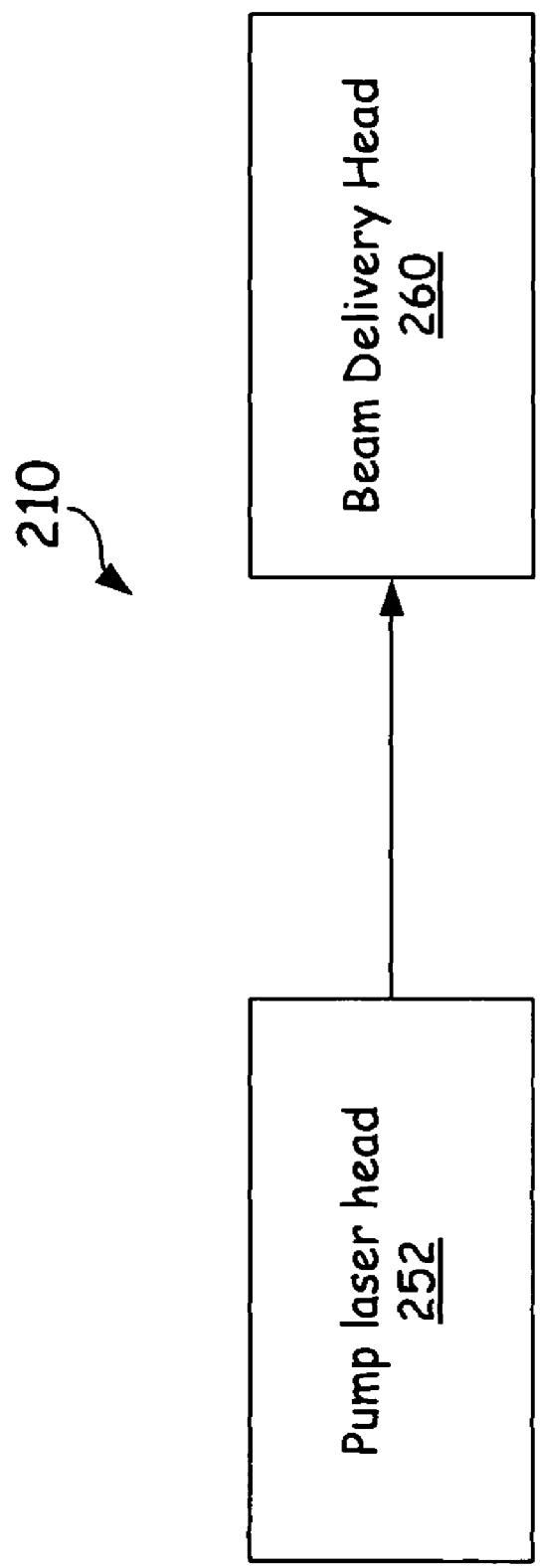
FIGS. 3A and 3B depict embodiments of a compact mid-IR generation laser in accordance with embodiments of the present invention.

FIG. 3A depicts one embodiment of a compact mid-IR ultrasound generation laser in accordance with embodiments of the present invention. This generation laser provides a compact, high-average power mid-IR laser for ultrasound generation. As shown in FIG. 3A, this generation laser 210 includes a pump laser head 252, having a fiber laser therein, fiber coupled to a generation laser head 260.

Figure 3B:
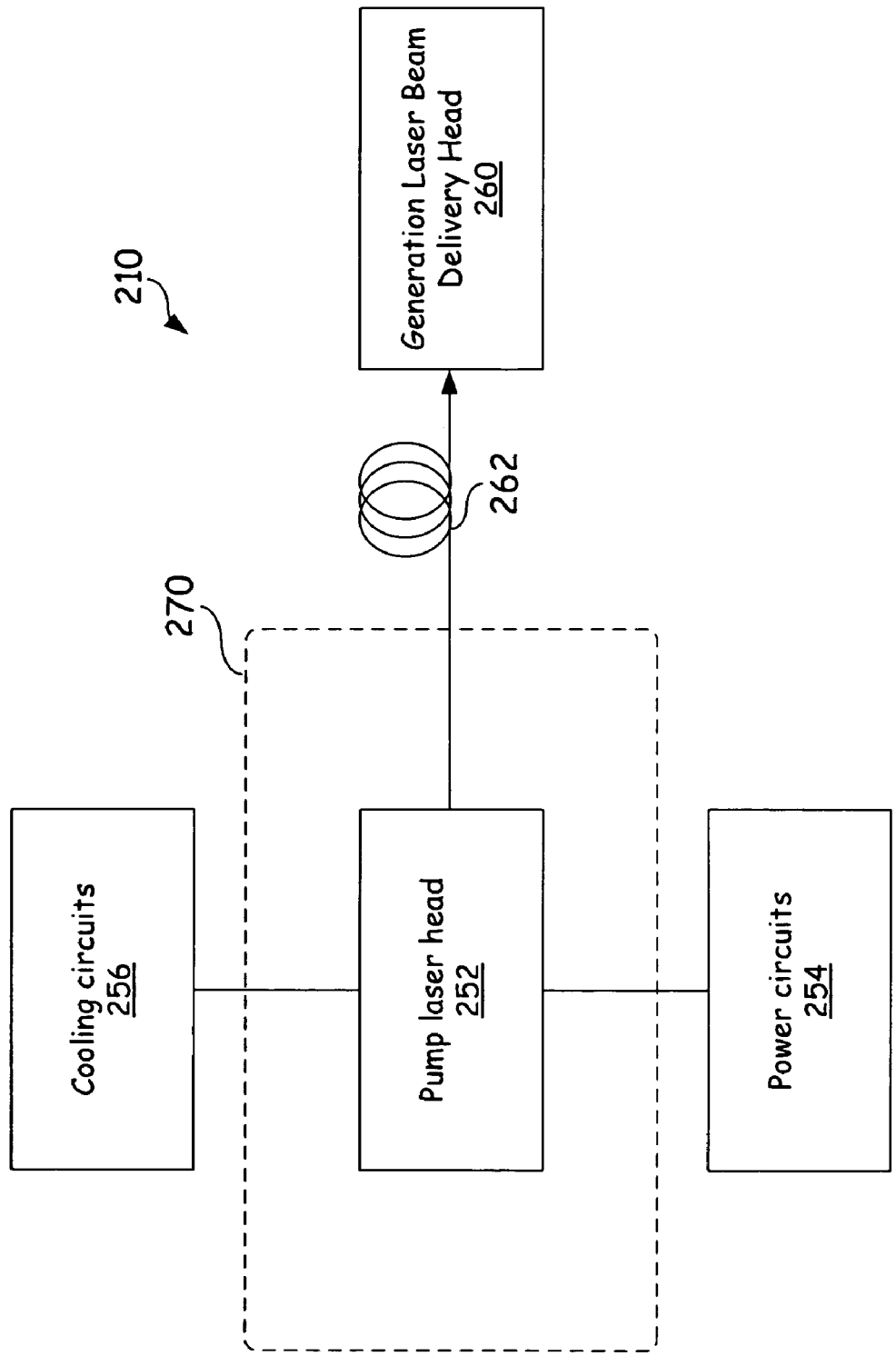

FIG. 3B provides another embodiment of generation laser 210. The generation laser 210 as depicted in FIG. 3B includes a pump laser head 252, power circuits 254, cooling circuits 256, optical fiber 262, and generation laser head 260. The pump laser head may utilize one or more fiber lasers. Using fiber lasers allows the laser pump to be located remotely from generation laser head 260. The pump laser head may be coupled via optical fiber 262 to the generation laser head 260.

Locating the pump laser head 252 meters away from generation laser beam delivery head 260 allows a compact mid-IR generation laser head since the overall payload and the stability requirements for robotic systems used to deliver the generation laser beam are significantly relaxed. Only a compact and light-weight module containing the generation laser beam delivery head is required to be mounted within the inspection head of the robotic system. This allows the deployment of a mid-IR laser source using smaller robots. Thus, new composite inspection opportunities are created for in-field composite NDE using portable laser ultrasound systems.

Several approaches are available to implement Thulium fiber lasers as the pump laser head for the Q-switched pulsed Holmium laser in the Mid-IR generation laser head within laser ultrasound systems. These approaches are distinguished in the manner in which the Thulium fiber laser is itself pumped. One approach uses an Erbium (ER) fiber laser stage pumped by fiber coupled single emitter laser diodes to pump the Thulium fiber laser—to produce the desired output, pump laser beam at a wavelength of about 1.9 microns. A second Thulium fiber laser design pumps the Thulium fiber laser directly with pump diodes (either in bar arrays or a collection of single emitter devices) operated at a wavelength of about 0.79 microns to produce desired output at a wavelength of about 1.9 microns. Downstream of the Thulium fiber laser, the generation laser head provides a mid-IR laser ultrasound source. The output beam of the Thulium fiber laser, laser beam 276, may be used as the input pump for a Q-switched pulsed laser stage, such as a Q-switched Holmium laser stage, in the generation laser head, as will be described in further detail with reference to FIGS. 5A and 5B. This Q-switched Holmium pulsed laser stage produces a pulsed laser output that is subsequently converted in the generation laser head to a mid-IR wavelength that may be used to more efficiently generate ultrasound in composite materials. The Q-switched Holmium laser in the generation laser head can be made of any Holmium doped material like Ho:YAG or Ho:YLF. Other variations of this Q-switched laser might possibly use co-doped material like Ho:Tm:YLF or Ho:Tm:YAG or any other co-dopant besides Thulium.

Figure 4A:
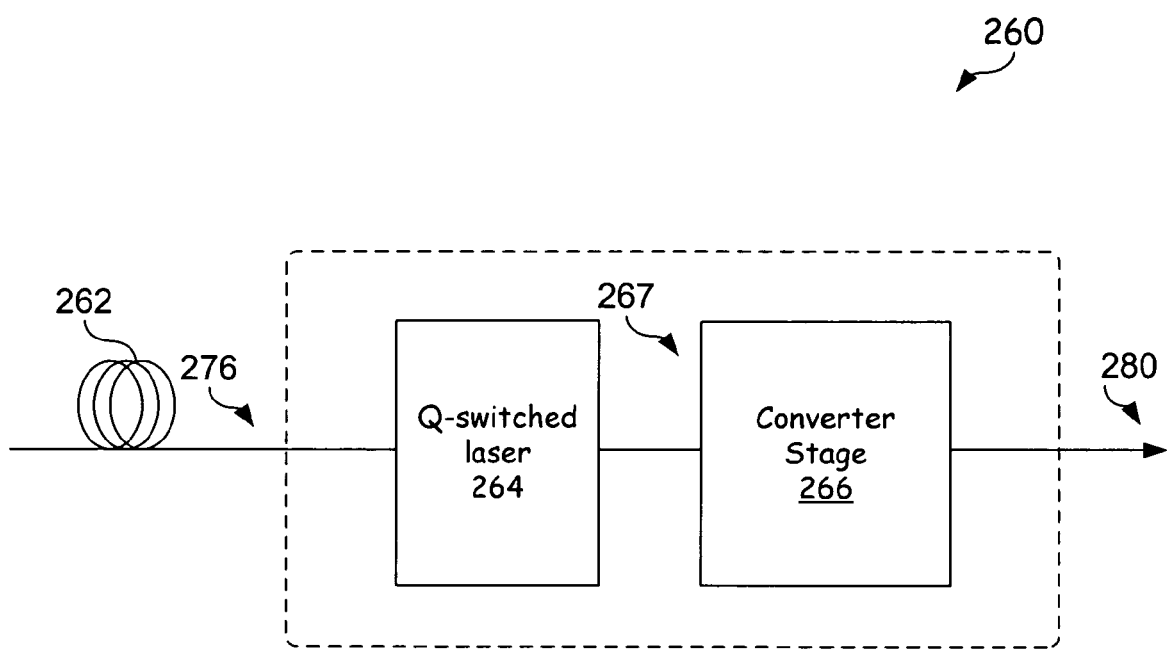
FIGS. 4A and 4B depict embodiments of the generation laser beam delivery head (converter stage) of FIGS. 3A and 3B in further detail.
Figure 4B:
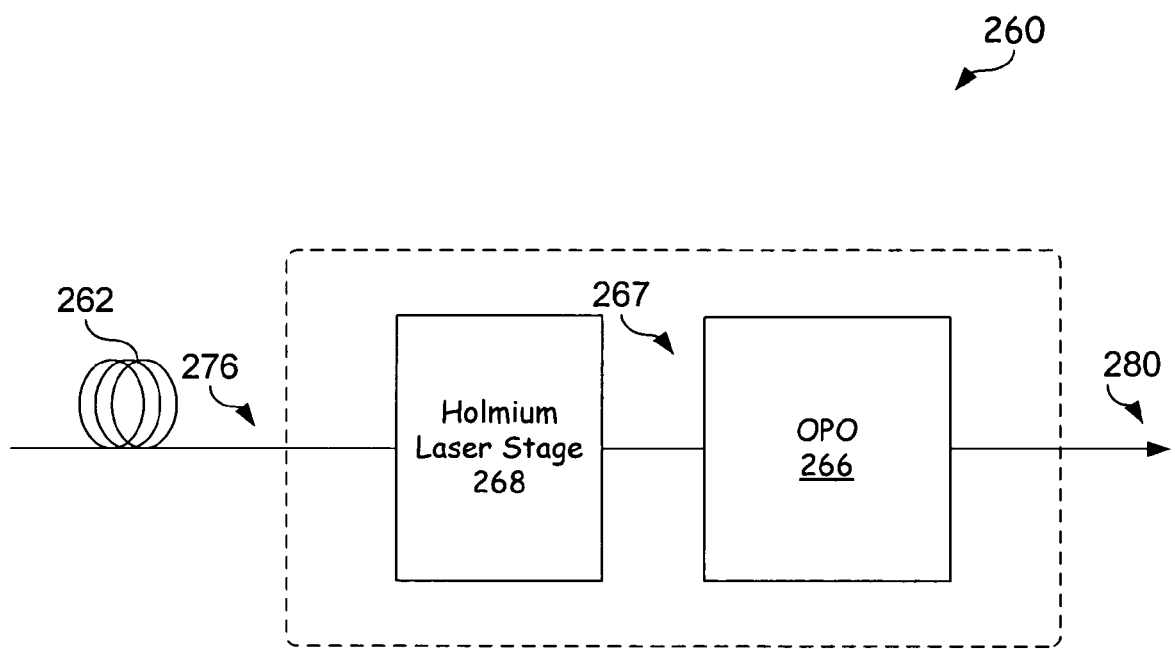

FIG. 4A depicts an embodiment of the generation laser beam delivery head 260 in accordance with embodiments of the present invention. As shown here, generation laser head 260 provides a compact laser head that drastically reduces the overall payload and stability requirements of the robotic system to which it is attached. Generically, the generation laser head includes a Q-switched laser stage 264 and a converter stage 266. The Q-switched laser stage receives the pump laser beam 276 from the pump laser stage to produce pulsed generation laser beam 267. Thus the Q-switched laser stage 264 produces a second longer wavelength as well as producing a Q-switched pulsed output from continuous, quasi continuous or pulsed input of the pump laser. Notice that in one embodiment, the pump laser head can be a Q-switched fiber laser producing directly the pulse laser beam required by the converter stage 266. In this embodiment, the Q-switched laser stage 264 would be part of the pump laser head 252 and the generation laser head would be comprised of only the converter stage 266. FIG. 4B depicts another embodiment of generation laser stage 260 that includes two distinct stages, a Q-switched Holmium laser 264 and a converter stage composed of a combination of one or more optical parametric oscillators (OPO's) and/or optical parametric amplifiers (OPA's) 266. Q-switched laser stage 264 is fiber-coupled or otherwise optically coupled to the beam delivery fiber 262 to receive the pump beam 276 from the Thulium pump laser. Because the bulk of any mid-IR laser system is associated with the Thulium pump laser, the fiber laser architecture provided within embodiments of the present invention greatly enhances the ability to provide a compact generation laser. Q-switched laser stage 264 may be a Q-switched laser stage producing output pulses of approximately 20 nano-seconds in width. The output of the Q-switched laser stage 264, laser beam 267, is then directed to the converter stage 266 which might consist of a zinc germanium phosphide (ZGP) optical parametric oscillator (OPO) 266 tuned to provide generation laser beam 280 having a desired mid-IR wavelength in the range of 3-4 microns. The converter stage 266 may also consist of any combination of OPO(s) and/or OPA(s) in series or parallel that allow the wavelength and power of the generation laser beam to be further controlled.

Pulse laser sources operating at mid-IR wave lengths in the range of 2-5 microns generate ultrasound effectively within a wide variety of engineering composite materials. Unfortunately for industrial implementations, a high-power Q-switched laser beam at 3-4 micron wave length is not readily transmitted through optical fibers. Therefore, embodiments of the present invention generate a first pump laser beam at a shorter wave length that is readily transmitted by commercial optical fibers. This pump laser beam is then delivered through an optical fiber to pump the Q-switched laser in the generation laser head 260. In one embodiment of the present invention, a diode pumped Thulium continuous wave (CW) or quasi-CW laser stage within pump laser head 252 emits a first pump laser beam 276 of about 1.9 microns which is used as the pump beam for Q-switched Holmuim laser stage 268. Q-switched Holmium laser stage 268 then emits a Q-switched pulsed laser beam having a wave length of about 2.1 microns. This Holmium laser beam may be used directly as the generation laser beam or serve as the pump beam for the ZGP OPO that is tuned to emit the desired mid-IR signal wave lengths in the range of 3-4 microns for having improved ultrasound generation efficiency within composite materials.

By fiber-coupling pump laser head 252 to generation laser head 260 key advantages are realized. For example, when the pump laser head employs a Thulium laser output having a wave length of about 1.9 microns, this output would be strongly absorbed by moisture in the atmosphere. To properly test composite materials and deliver an appropriate generation laser, the use of conventional Thulium laser modules required that the moisture content of the atmosphere be kept below a 10 percent relative humidity value which may have involved purging the atmosphere with dry inert gas. Alternatively, additional system complexity may have been introduced by hermetically sealing inspection enclosures and regular replenishment of the inert gas. If humidity in the Thulium laser cavity became too high, the Thulium laser, itself, can Q-switch resulting in high peak powers that can damage the Thulium crystal requiring replacement. Using a Thulium fiber laser 252 to pump the Q-switched Holmium laser eliminates this potential failure mechanism, since the laser cavity is completely confined within clad optical fibers. There is no interaction between the laser and the atmosphere. This eliminates the need to hermetically seal the laser pathway.

Furthermore, contributing to greater robustness associated with embodiments of the present invention are that single emitter 960 nm telecom laser diodes used within some embodiments of the present invention are commercially available. These devices have demonstrated greater reliability than laser diode bar arrays. Furthermore, should a pump diode within the fiber laser fail, the affect on the overall output of the fiber laser is negligible and replacement is straightforward. Additionally, the power requirements supplied by power circuits 254 and cooling requirements supplied by cooling circuits 256 are greatly reduced when compared to prior configurations which employed Thulium slab lasers to generate the pump laser beam for the Q-switched Holmium laser.

Prior laser ultrasound inspection systems employed high-average power pulse mid-IR generation lasers. This high-average power pulsed mid-IR laser was extremely large where the size was driven by the Thulium:YLF laser and associated cooling and power supplies necessary to operate the Thulium:YLF laser. Because the fiber pump laser allows thermal energy to be more readily removed and has an improved ratio of surface area to volume, the cooling problems and resulting thermal distortion problems associated with prior Thulium slab lasers are reduced or eliminated.

Figure 5:
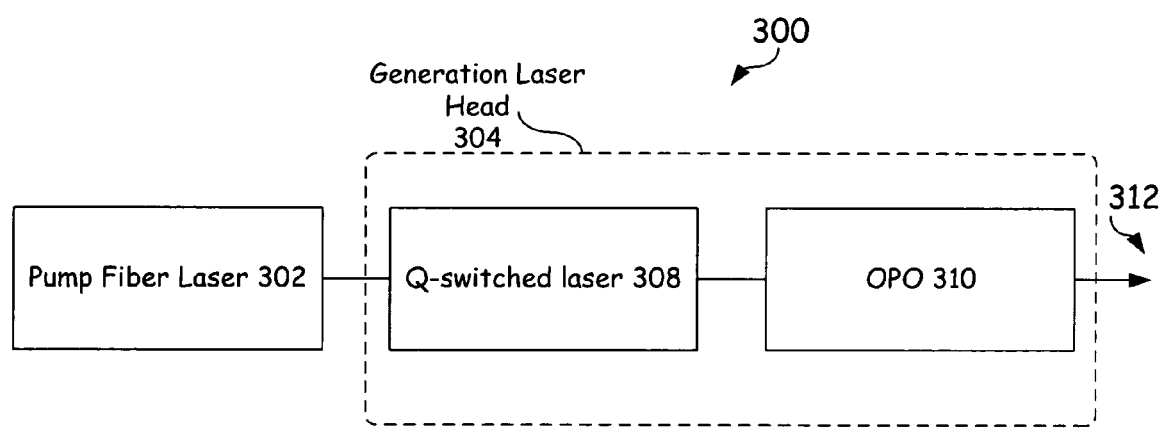
FIG. 5 generically depicts an embodiment of a mid-IR fiber based generation laser configuration in accordance with embodiments of the present invention.

FIG. 5 generically depicts an embodiment of a mid-IR fiber based generation, laser configuration in accordance with embodiments of the present invention. Mid-IR fiber based laser 300 includes a fiber pump laser 302, and generation laser head stage 304 (including Q-switched laser 308 and OPO 310) to generate a mid-IR light emission for ultrasound generation 312. These elements are optically coupled as follows. The output of fiber pump laser 302 may be fiber coupled to Q-switched laser 308 in generation laser head 304. The output from Q-switched laser 308 serves as the input pump beam for OPO 310 to produce pulsed generation laser beam 312. This allows a more compact generation laser that is less susceptible to atmospheric distortion and contamination, thus offering more reliable performance for production inspection applications.

Figure 6A:
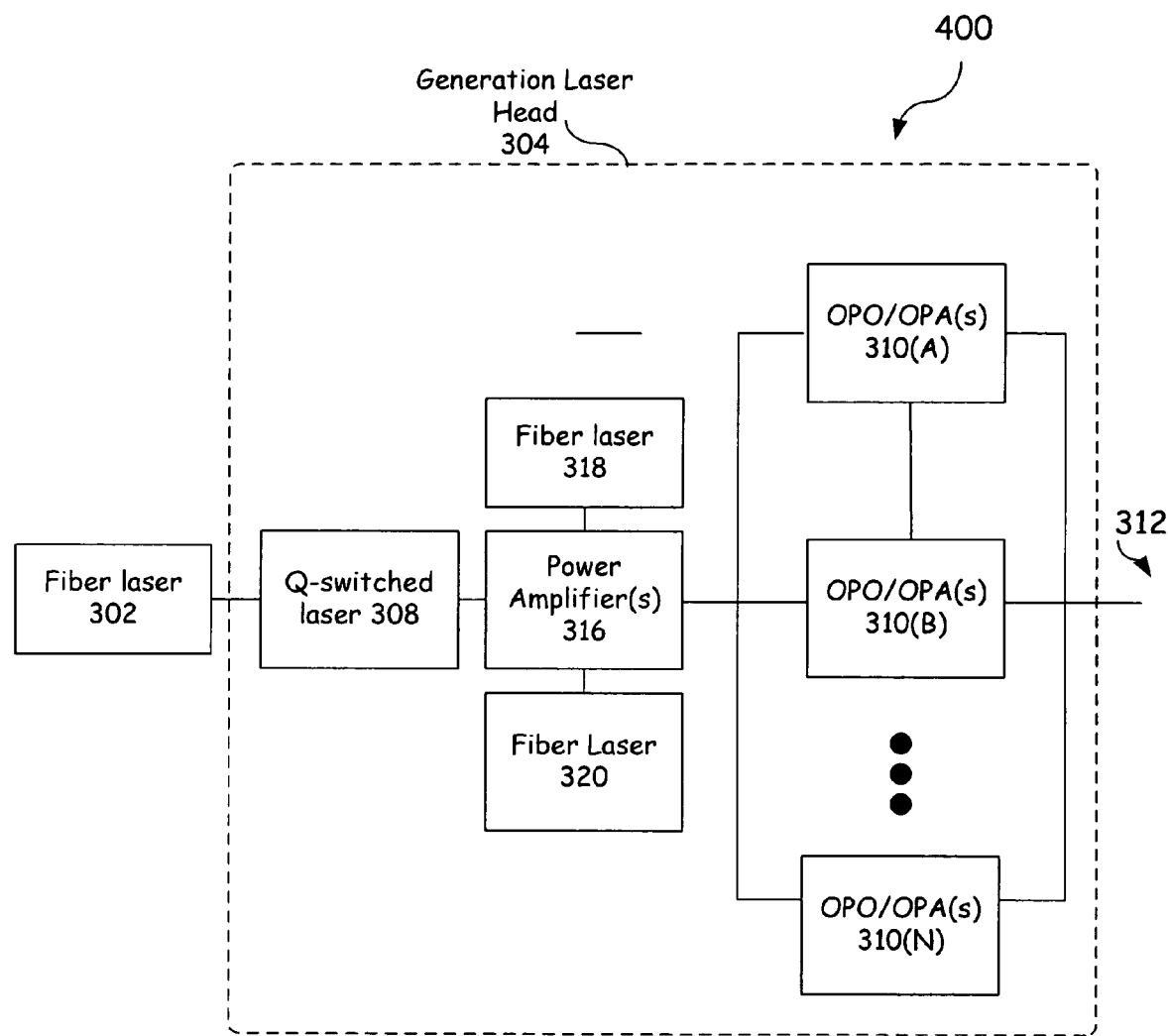
FIGS. 6A and 6B depicts other fiber based mid-IR laser configurations operable to provide larger pulse energies in accordance with embodiments of the present invention.
Figure 6B:
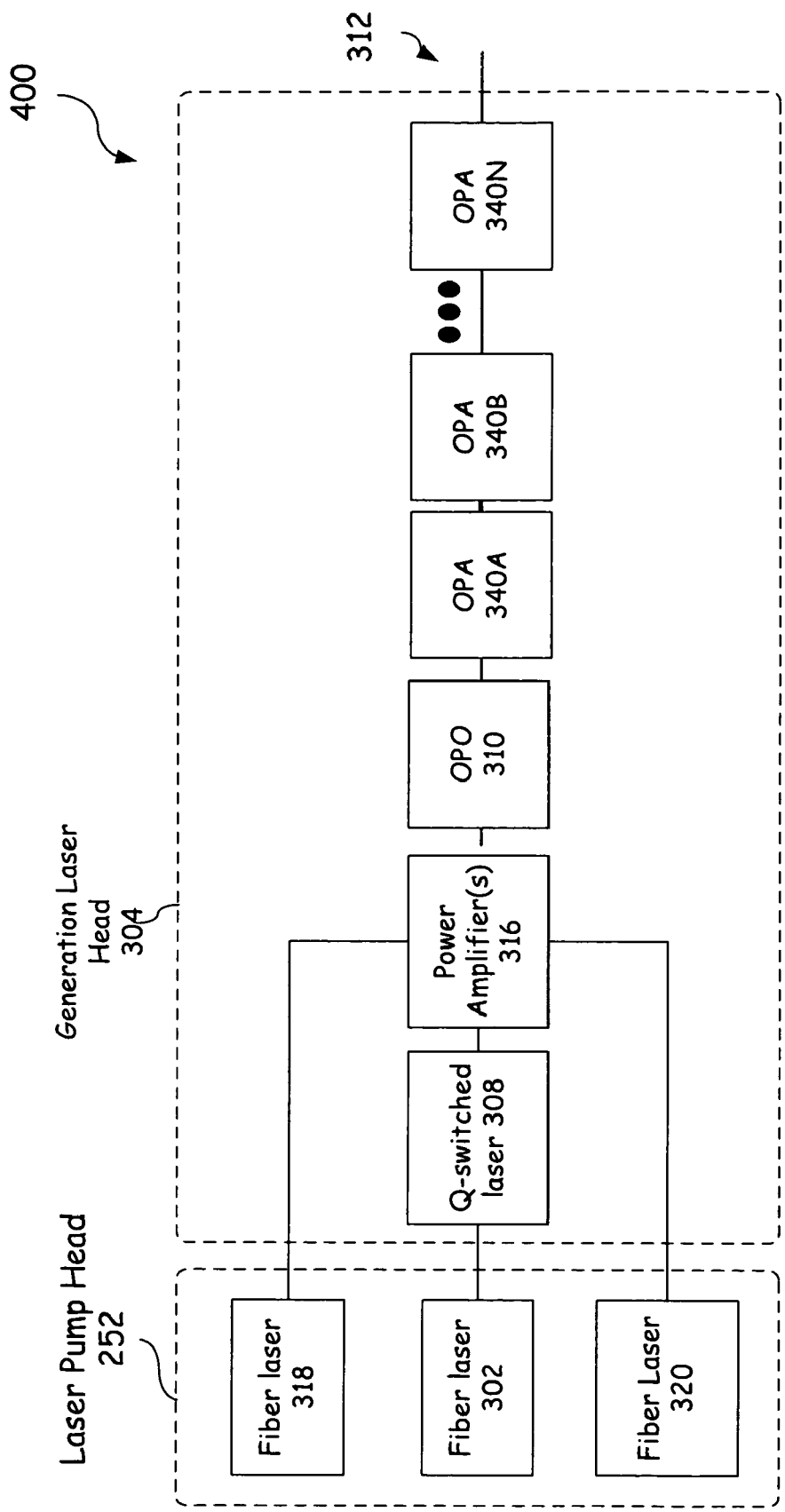

FIGS. 6A and 6B depict embodiments of a fiber based mid-IR laser configuration 400 operable to provide larger pulse energies in accordance with embodiments of the present invention. This fiber based mid-IR laser configuration includes a pump laser head 252 comprising pump fiber lasers 302, 318 and 320, and generation laser head 304. Generation laser head 304 further includes Q-switch laser 308, power amplifier(s) 316 driven by additional fiber pump lasers 318 and 320, one or more OPO(s) 310 and OPA(s) 340, in series or parallel. FIG. 6A depicts an embodiment of parallel OPO/OPA(s) 340 while FIG. 6B depicts an embodiment of OPO and OPA(s) in series. In this embodiment a fiber laser or a combination of fiber laser(s) 302 pump the Holmium oscillator and Holmium amplifier stages in generation laser head 304. Specifically fiber laser 302 pumps the Q-switched Holmium laser oscillator stage 308. The output of the Q-switched Holmium laser oscillator stage 308 is sent to a single or series of Holmium power amplifier(s) 316. These Holmium power amplifier(s) 316 may be pumped by a similar combination of fiber lasers 318 and 320. The output of the power amplifiers is provided to one or more OPOs 310 and OPAs 340. The one or more OPO might be designed to compensate for beam distortion, very often encountered in high-power OPOs. One approach to significantly improve the beam quality at the output of the OPO is to include an image-rotating feature in the OPO. This approach is similar to that within the Rotated Image Singly-Resonant Twisted RectAngle (RISTRA) designed by Sandia National Laboratory. This approach is described in "*Nanosecond optical parametric oscillator with 90° mage rotation: design and performance*," by Arlee V. Smith and Darrell J. Armstrong, Vol. 19, No. 8, Aug. 2002/J. Opt. Soc. Am. B which is incorporated by reference.

In the series configuration, the OPO 310 produces the laser beam at the desired wavelength. The following series of OPAs 340 amplifies that beam, bringing it to the required energy levels for the output beam 312. This approach has the advantage of being scalable just by increasing the number of OPAs 340 with the adequate number of pump fiber lasers and power amplifiers.

Similar fiber laser technology may be combined with and applied to the detection laser as well. Such a fiber laser detection laser is disclosed in U.S. patent application Ser. No. 11/458,377, entitled "FIBER LASER FOR ULTRASONIC TESTING" filed on Jul. 18, 2006 which is incorporated by reference in its entity for all purposes.

Figure 7:
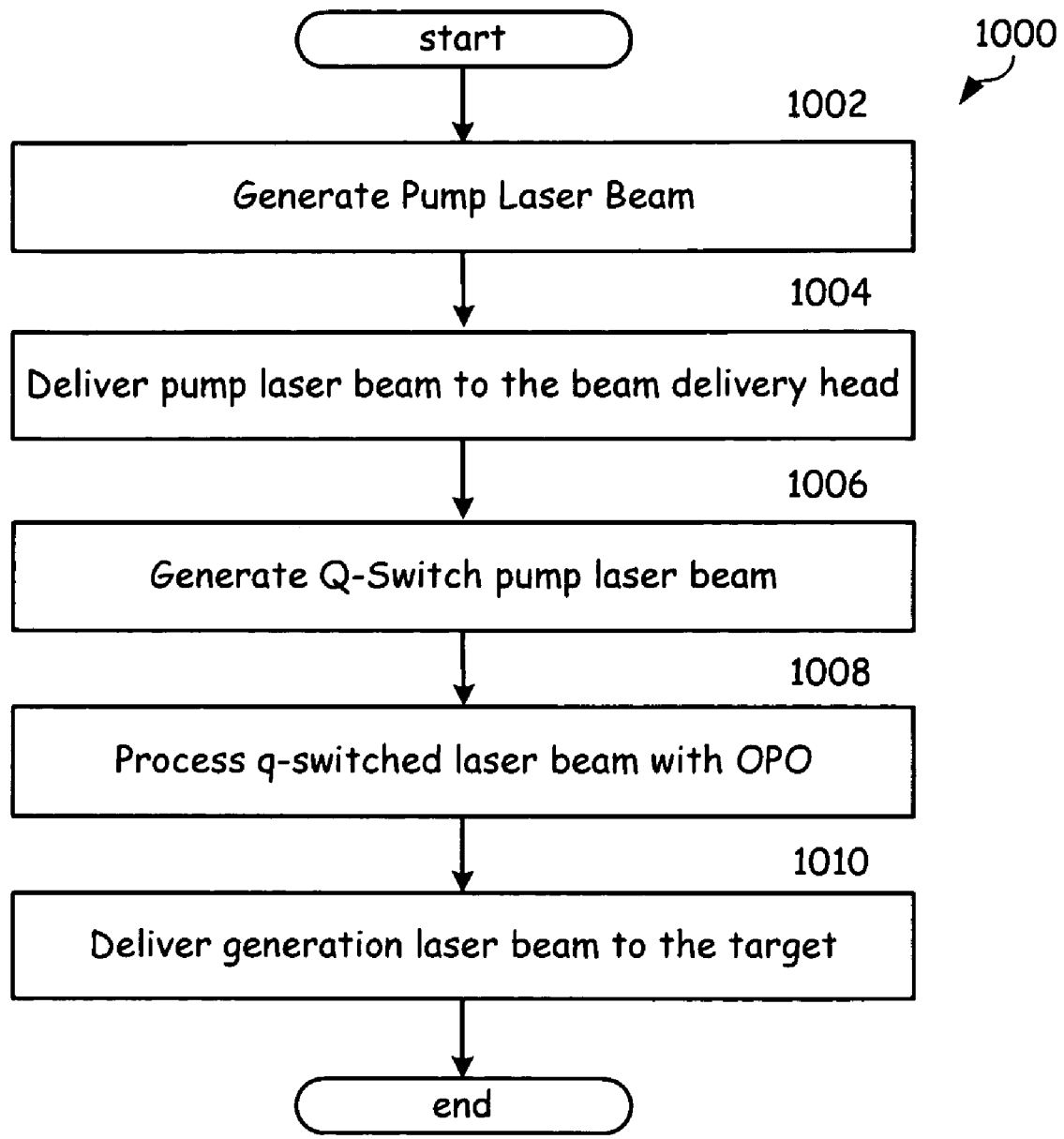
FIG. 7 provides a logic flow diagram in accordance with one or more embodiments of the present invention.

FIG. 7 provides a logic flow diagram in accordance with one or more embodiments for the present invention that depict how a compact mid-IR generation laser can be generated within a laser ultrasound inspection system. Operations 1000 began with the generation of a fiber pump, laser beam in Step 1002. In step 1004 the pump laser beam is delivered to the generation laser beam delivery head. This pump laser beam drives a Q-switched laser in step 1006 to create a pulsed laser output. Then in step 1008 the wavelength may be further tuned to a more desirable wavelength using OPO(s) and/or OPA(s) to generate a generation laser beam with the desired properties for laser ultrasound. In step 1010 the generation laser beam is delivered to the target.

In operation the present invention allows laser ultrasonic test equipment to be used in a wider range of environments while testing more complex surfaces or surfaces within limited access areas. The embodiments of the present invention may utilize fiber lasers to generate and deliver generation laser beams to a remote target to be tested. Doing so allows the overall size of a laser ultrasound system to be greatly reduced. For example, instead of a large gantry robotic based system, a much smaller robotic system may be used to deliver generation and detection laser beams to the surface of the target to be tested. This allows the laser ultrasound inspection system offered by embodiments of the present invention to be used to not only inspect individual components but to assess the internal structure of integrated components. Thus, not only can individual parts be inspected by the laser ultrasound system offered by embodiments of the present invention but assembled structures made from individual parts may be inspected. This allows inspections to be made after the integrated structure has been built to determine if changes in the internal structure over the life of the structure have occurred. Additionally, embodiments of the present invention may provide an entirely mobile system that uses fiber lasers to generate and detect ultrasonic displacements at a remote target in the field without the problems often associated with free space delivery of generation and detection laser beam(s).

Fiber lasers and fiber amplifiers can be pumped using different approaches. The most popular approach is cladding-pumping where the pumping radiation is inserted in the cladding of the fiber laser or amplifier. Cladding pumping can be done either from the cladding end (end pumping) or the cladding side (side-pumping). Side-pumping eliminates the difficulties of end or coaxial pumping, with off-axis core designs or twisted active and pump fiber designs. In addition, a fused-fiber coupling eliminates the need for focusing optics and alignment, and is more robust than other designs such as end or V-groove pumping By employing individual diodes and a cladding side-pumping technology, the power can be scaled up by the introduction of additional pump diodes with no adverse effect on reliability. The lifetime of the individual diodes is orders of magnitude larger that of diode bars. Additionally, single emitter pump diodes are independent from each other and the failure of one pump diode does not affect any other pump diode, contrarily to diode bars where the entire diode array ceases operation when a single diode bar fails. Finally, in case of the failure of a single emitter, the decrease in total output power of the fiber laser or amplifier is very small because of the large number of diode emitters.

In summary, the embodiments of the present invention relate to a laser system and method for the optical generation of ultrasound at a remote target. This involves generating a pump laser beam with a fiber pump laser head. The pump laser head may be fiber coupled to the generation laser head. The generation laser head produces a pulsed generation laser beam from the pump laser beam and directs the generation laser beam to the surface of the remote target. The interaction between generation laser beam and the surface of the remote target results in ultrasonic displacements at the remote target. These ultrasonic displacements may be sampled in order to assess and inspect the remote target.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A method to generate ultrasonic surface displacements at a remote target comprising:

generating a pump laser beam with a diode-pumped fiber laser pumping a generation laser with the diode-pumped fiber laser; and directing the generation laser beam to a surface of the remote target, wherein the generation laser beam produces ultrasonic displacements at the remote target.

2. The method of claim 1, wherein the generation laser is located in a generation laser head that comprises a Q-switched laser stage and an optical parametric oscillator (OPO) stage, wherein the Q-switched laser stage receives the pump laser beam to produce a laser beam that is converted by the OPO stage into a generation laser beam.

3. The method of claim 2, wherein the Q-switched laser is comprised of an oscillator followed by power amplifiers.

4. The method of claim 2, wherein the OPO stage is combined with optical parametric amplifiers (OPA) to increase the output generation laser beam energy.

5. The method of claim 2, wherein the OPO stage comprises an image-rotating feature to improve beam quality of the generation laser beam.

6. The method of claim 2, wherein the Q-switched laser is either a separate stage inside the generation laser head or is directly in the pump laser beam as part of the diode-pumped fiber.

7. The method of claim 1, further comprising:
generating a detection laser beam;
directing the detection laser beam to the surface of the remote target;
scattering the detection laser beam at the surface of the remote target to produce light phase-modulated by ultrasonic surface displacements;
collecting the phase modulated light;
processing the phase modulated light to obtain data representative of the ultrasonic surface displacements at the surface; and
collecting the data with the information to analyze structures within the remote target.

8. The method of claim 1, wherein fiber-coupling the diode pumped fiber laser to generation laser head uses the active laser fiber.

9. An apparatus operable to generate ultrasonic surface displacements on a remote target comprising:
a diode pumped fiber laser
a generation laser head fiber-coupled to the diode pumped fiber laser operable to:
generate a generation laser beam from the pump laser beam; and
direct the generation laser beam to a surface of the remote target, wherein the generation laser beam produces ultrasonic displacements at the remote target.

10. The apparatus of claim 9, wherein the generation laser is located in a beam delivery head that comprises a Q-switched laser stage and an optical parametric oscillator (OPO) stage, wherein the Q-switched laser stage receives the pump laser beam to produce a laser beam that is converted by the OPO stage into a generation laser beam.

11. The apparatus of claim 10, wherein the coupling of the diode pumped fiber laser and the beam delivery head comprises a passive optical fiber.

12. The apparatus of claim 10, wherein the coupling of the diode pumped fiber laser and the beam delivery head is obtained through the active fiber of the fiber laser.

13. The apparatus of claim 10, further comprising: a detection laser operable to generate a detection laser beam that substantially illuminates the ultrasonic surface displacements at the remote target;
collection optics, optically coupled to a scanning optical assembly, operable to collect phase modulated light from the diode pumped detection fiber laser either reflected or scattered by the remote target; and a processor operable to:
process the phase modulated light from the diode pumped detection fiber laser either reflected or scattered by the remote target to obtain data representative of the ultrasonic displacements at the remote target;
process the data representative of the ultrasonic displacements to assess the structural integrity of the remote target; and
a laser ultrasound detection system operable to detect ultrasonic displacements at the remote target.

14. A large area composite inspection apparatus to generate ultrasonic surface displacements on a surface of a remote target comprising:
a pump laser head comprising a diode pumped fiber laser, an optical fiber,
a generation laser head fiber-coupled to the diode pumped fiber with the optical fiber wherein the generation laser head is operable to:
generate a generation laser beam from the pump laser beam; and
direct the generation laser beam to a surface of the remote target, wherein the generation laser beam produces ultrasonic displacements at the remote target.

15. The large area composite inspection apparatus of claim 14, further comprising:
a detection laser operable to illuminate ultrasonic surface displacements on the surface of the remote target with a detection laser beam;
a scanning optical assembly operable to scan the detection laser beam across the surface of the remote target;
collection optics, optically coupled to the scanning optical assembly for collecting phase modulated light from the detection laser beam either reflected or scattered by the remote target;
an optical processor to process the phase modulated light collected by the collection optics and produce an output signal; and
a processor operable to process the output signal to obtain data representative of the ultrasonic surface displacements on the surface of the remote target.

16. The large area composite inspection apparatus of claim 15, wherein the detection laser beam comprises a continuous wave mode laser beam or a pulsed laser beam.

17. The large area composite inspection apparatus of claim 15, wherein the detection laser comprises:
a master oscillator operable to generate a seed laser beam; and
at least one diode pumped laser amplifier operable to amplify the seed laser beam, wherein at least the master oscillator or the at least one diode pumped laser amplifier comprises diode pumped fiber.

18. The large area composite inspection apparatus of claim 17, wherein the master oscillator or the at least one diode pumped laser amplifier of the detection laser comprises a diode pumped slab laser.

19. The large area composite inspection apparatus of claim 15, further comprising a scanning optical assembly to move the generation laser across the surface of the remote target and then record and index the data detected by the large area composite inspection apparatus.

20. The large area composite inspection apparatus of claim 19, wherein a positioning apparatus comprises a large gantry system and/or a compact robotic system.

* * * * *